US010899829B2

(12) United States Patent
Bogatcheva et al.

(10) Patent No.: US 10,899,829 B2
(45) Date of Patent: Jan. 26, 2021

(54) EMAPII NEUTRALIZING ANTIBODY LIMITS INFLUENZA A VIRUS (IAV)-INDUCED LUNG INJURY

(71) Applicant: INDIANA UNIVERSITY RESEARCH & TECHNOLOGY CORPORATION, Indianapolis, IN (US)

(72) Inventors: Natalia Bogatcheva, Westfield, IN (US); Matthias Alexander Clauss, Indianapolis, IN (US); Keith L. March, Carmel, IN (US)

(73) Assignees: INDIANA UNIVERSITY RESEARCH AND TECHNOLOGY CORPORATION, Indianapolis, IN (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/078,873

(22) PCT Filed: Feb. 23, 2017

(86) PCT No.: PCT/US2017/019069
§ 371 (c)(1),
(2) Date: Aug. 22, 2018

(87) PCT Pub. No.: WO2017/147258
PCT Pub. Date: Aug. 31, 2017

(65) Prior Publication Data
US 2019/0153087 A1 May 23, 2019

Related U.S. Application Data

(60) Provisional application No. 62/298,703, filed on Feb. 23, 2016, provisional application No. 62/403,280, filed on Oct. 3, 2016.

(51) Int. Cl.
A61K 39/00 (2006.01)
A61K 39/395 (2006.01)
C07K 16/24 (2006.01)
A61P 11/00 (2006.01)
A61P 29/00 (2006.01)
A61K 45/06 (2006.01)

(52) U.S. Cl.
CPC .......... *C07K 16/24* (2013.01); *A61K 39/3955* (2013.01); *A61K 45/06* (2013.01); *A61P 11/00* (2018.01); *A61P 29/00* (2018.01); *A61K 2039/505* (2013.01); *C07K 2317/55* (2013.01); *C07K 2317/76* (2013.01)

(58) Field of Classification Search
None
See application file for complete search history.

(56) References Cited

U.S. PATENT DOCUMENTS

| 5,565,354 A | 10/1996 | Ostberg |
| 5,567,310 A | 10/1996 | Borrebaeck |
| 5,569,825 A | 10/1996 | Lonberg |
| 5,571,893 A | 11/1996 | Baker |
| 2010/0247538 A1* | 9/2010 | Elias ............... A61K 31/00 424/135.1 |
| 2011/0111064 A1 | 5/2011 | Nerome |
| 2014/0221607 A1 | 8/2014 | Clauss |
| 2015/0037320 A1 | 2/2015 | McGrath |
| 2016/0009768 A1 | 1/2016 | Davis |

FOREIGN PATENT DOCUMENTS

| EP | 0239400 | 3/1987 |
| WO | 9204381 | 3/1992 |
| WO | WO-2012170929 A2 * | 12/2012 ......... C07K 16/2866 |

OTHER PUBLICATIONS

Tuder et al. Pathogenesis of chronic obstructive pulmonary disease. J Clin Invest. 2012;122(8):2749-2755. (Year: 2012).*
Kang et al. Cigarette smoke selectively enhances viral PAMP- and virus-induced pulmonary innate immune and remodeling responses in mice. J. Clin. Invest. 118:2771-2784 (2008). (Year: 2008).*
Clauss et al. Neutralization of EMAP II inhibits cigarette smoke-induced lung emphysema. American Journal of Respiratory and Critical Care Medicine, (May 1, 2010) vol. 181, No. 1, Supp. Meeting Abstract # A5059). (Year: 2010).*
Liang et al. AIMp1 Potentiates TH1 Polarization and Is Critical for Effective Antitumor and Antiviral Immunity. Front Immunol. Jan. 15, 2018;8:1801. (Year: 2018).*
Lu et al. EMAPII Monoclonal Antibody Ameliorates Influenza A Virus-Induced Lung Injury. Molecular Therapy vol. 26 No. 8 Aug. 2018 (Year: 2018).*
Barik, New treatments for influenza. BMC Medicine 2012; 10: 104.
Barnett, et al., Prostate adenocarcinoma cells release the novel proinflammatory polypeptide EMAP-II in response to stress. Cancer research 2000; 60: 2850-2857.
Boerner P et al., Production of antigen-specific human monoclonal antibodies from in vitro-primed human splenocytes. J Immunol 1991; 147:86-95.
Brodeur et al., Monoclonal Antibody Production Techniques and Applications, pp. 51-63 (Marcel Dekker, Inc, New York, 1987)—book.

(Continued)

*Primary Examiner* — Maher M Haddad
(74) *Attorney, Agent, or Firm* — Quarles & Brady LLP

(57) ABSTRACT

EMAPII is a monocyte- and endothelial cell-activating protein with prominent pro-apoptotic activity on endothelial and epithelial cells. Provided herein are compositions and methods for treating or preventing endothelial and epithelial apoptosis induced by EMAPII. More particularly, provided herein are compositions and methods for treating or preventing Influenza A virus (IAV)-induced weight loss, impairment of blood oxygenation, lung edema, and endothelial/epithelial apoptosis associated with IAV infections. In addition, anti-EMAPII therapy provides a novel complementary treatment strategy to existing anti-viral and anti-inflammatory approaches.

15 Claims, 8 Drawing Sheets

Specification includes a Sequence Listing.

(56) References Cited

OTHER PUBLICATIONS

Bruggermann et al., Designer mice: the production of human antibody repertoires in transgenic animals. Year in Immunology 1993; 7:33-40.
Clauss, et al., Lung endothelial monocyte-activating protein 2 is a mediator of cigarette smoke-induced emphysema in mice. The Journal of clinical investigation 2011; 121: 2470-2479.
D'Alessio, et al., CD4+CD25+Foxp3+ Tregs resolve experimental lung injury in mice and are present in humans with acute lung injury. The Journal of clinical investigation 2009; 119: 2898-2913.
D'Alessio, et al., Enhanced Resolution of Experimental ARDS through IL-4-Mediated Lung Macrophage Reprogramming. Am J Physiol Lung Cell Mol Physiol 2016: ajplung.00419.02015.
Ecker, et al., The therapeutic monoclonal antibody market. mAbs 2015; 7: 9-14.
Green, et al. HIV envelope protein gp120-induced apoptosis in lung microvascular endothelial cells by concerted upregulation of EMAP II and its receptor, CXCR3. Am J Physiol Lung Cell Mol Physiol 2014; 306: L372-382.
Hayden, et al., Emerging influenza antiviral resistance threats. The Journal of infectious diseases 2011; 203: 6-10.
Hsu, et al., Antivirals for treatment of influenza: a systematic review and meta-analysis of observational studies. Annals of internal medicine 2012; 156: 512-524.
ISR and Written Opinion for PCT/US17/19069, dated May 18, 2017.
Jakobovits, et al., Analysis of homozygous mutant chimeric mice: Deletion of the immunoglobulin heavy-chain joining region blocks B-cell development and antibody production. Proc Natl Acad Sci USA 1993; 90:2551-5.
Jakobovits, et al., Germ-line transmission and expression of a human-derived yeast artificial chromosome. Nature 1993; 362:255-8.
Knies, et al., Regulation of endothelial monocyte-activating polypeptide II release by apoptosis. Proc Natl Acad Sci U S A 1998; 95: 12322-12327.
Kozbor, et al., A human hybrid myeloma for production of human monoclonal antibodies. J Immunol 1984; 133:3001-5.
Mertz, et al., Populations at risk for severe or complicated influenza illness: systematic review and meta-analysis. BMJ (Clinical research ed) 2013; 347: f5061.
Nair, et al. Global burden of respiratory infections due to seasonal influenza in young children: a systematic review and meta-analysis. Lancet (London, England) 2011; 378: 1917-1930.
Rajashekhar, et al., A monoclonal rat anti-mouse EMAP II antibody that functionally neutralizes pro- and mature-EMAP II in vitro. J Immunol Methods 2009; 350(1-2):22-28.
Schwarz, et al., Endothelial-monocyte activating polypeptide II, a novel antitumor cytokine that suppresses primary and metastatic tumor growth and induces apoptosis in growing endothelial cells. The Journal of experimental medicine 1999; 190: 341-354.
Schwarz, et al., In vivo therapy of local tumor progression by targeting vascular endothelium with EMAP-II. J Surg Res, 2004. 120(1): p. 64-72.
Van der Vries, et al., Prolonged influenza virus shedding and emergence of antiviral resistance in immunocompromised patients and ferrets. PLoS pathogens 2013; 9: e1003343.
Ward, et al., Binding activities of a repertoire of single immunoglobulin variable domains secreted from *Escherichia coli*. Nature 1989; 341:544-546.
Zhang, et al., Comparison of the therapeutic effects of human and mouse adipose-derived stem cells in a murine model of lipopolysaccharide-induced acute lung injury. Stem Cell Res Ther 2013; 4: 13.

* cited by examiner

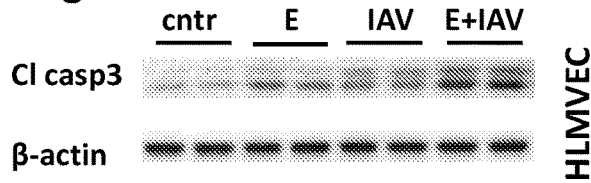
Fig. 2A
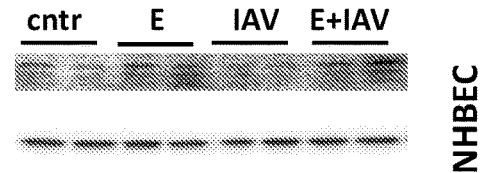
Fig. 2B
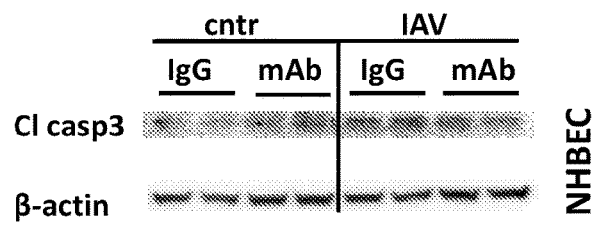
Fig. 2C
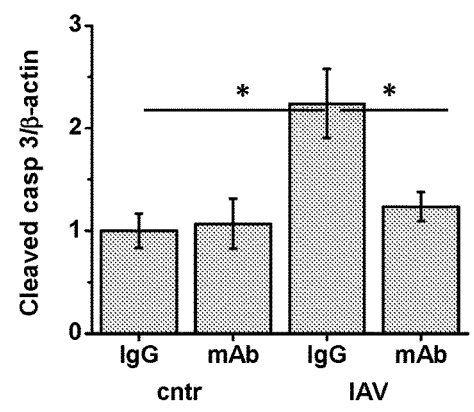

EMAPII NEUTRALIZING ANTIBODY LIMITS INFLUENZA A VIRUS (IAV)-INDUCED LUNG INJURY

CROSS-REFERENCE TO RELATED APPLICATIONS

This application represents the U.S. National Stage of International Application No. PCT/US2017/019069, filed Feb. 23, 2017, which claims priority to U.S. Provisional Applications No. 62/298,703 filed on Feb. 23, 2016 and 62/403,280 filed on Oct. 3, 2016, both of which are incorporated by reference in their entireties.

STATEMENT REGARDING FEDERALLY FUNDED RESEARCH

This invention was made with government support under HL129843 and TR000006 awarded by National Institutes of Health. The government has certain rights in the invention.

STATEMENT REGARDING FEDERALLY SPONSORED RESEARCH

This invention was made with government support under HL129843 and TR000006 awarded by National Institutes of Health. The government has certain rights in the invention The content of the ASCII text file of the sequence listing named "144578.00264_ST25.txt" which is 11.5 kb in size was created on Mar. 9, 2020 and electronically submitted via EFS-Web herewith the application is incorporated herein by reference in its entirety.

BACKGROUND

Nature of the disease and current unmet medical need.

Influenza virus infections represent major health and economic burden, with inter-pandemic influenza claiming close to 1 billion cases globally. Despite the use of anti-influenza vaccinations, influenza remains a highly spreadable disease leading to severe complications and mortality in groups with higher risk of complications, such as elderly and children. Retrospective studies show that in 2008 alone, 28 000 to 111 500 deaths in children younger than 5 years were attributed to influenza [1]. As of now, neuraminidase inhibitors seem to be fairly effective in reducing mortality and complications of influenza [2]; however, efficiency of these therapies is expected to be limited in the nearest future by almost inevitable selection of drug-resistant viral mutants [3]. Despite the development of influenza vaccines, efficiency of vaccination is often compromised by the constant change in circulating viruses. Antiviral drug efficiency is also limited by the developing resistance of influenza virus strains to antivirals. Although current resistance to oseltamivir and its analogues remains low, there is no guarantee that circulating viruses will not acquire resistance to neuraminidase inhibitors, like they did in the past to M2 ion channel blockers (rimantadine and analogues). Therefore, a therapy which would not be virus-specific, but rather increase the ability of lung to protect itself against virus-induced injury, is required to ascertain future success of therapeutic approaches to influenza-associated pneumonia and acute respiratory distress syndrome (ARDS).

Since acute lower respiratory infection remains leading cause of morbidity and mortality associated with influenza [1], it makes sense to develop a therapy that limits lung damage in a host in addition to existing therapies limiting viral replication processes. Major contributors to lung edema development include endothelial and epithelial barrier dysfunction resulting from increased endothelial and epithelial hyperpermeability, and endothelial and epithelial damage caused by apoptosis. Lung edema reduces the ability of the lungs to oxygenate blood. Whereas lung inflammation can be attenuated by steroids and other immunomodulators, there are currently no therapies for endothelial and epithelial lung damage.

BRIEF SUMMARY OF THE INVENTION

This disclosure provides antibodies, including a monoclonal antibody, having specificity for and that neutralizes a protein named EMAPII, which is secreted by lung epithelium and possibly other alveolar cells such as alveolar macrophages during Influenza A virus (IAV) infection and contributes to edema formation in the lung. Also provided herein are methods for treating or preventing edema formation, limiting vascular endothelial and epithelial cell death, and limiting vascular leakage.

In a first aspect, provided herein is a method of treating or preventing endothelial or epithelial lung damage, where the method comprises or consists essentially of administering a therapeutically effective amount of an EMAPII-neutralizing antibody to a subject having or suspected of having a lower respiratory tract influenza A virus infection, whereby endothelial or epithelial lung damage is treated or prevented. The endothelial or epithelial lung damage can be selected from the group consisting of weight loss, impairment of blood oxygenation, and lung edema. The EMAPII-neutralizing antibody can be co-administered with one or more agents selected from the group consisting of an anti-inflammatory agent and an anti-viral agent.

DESCRIPTION OF THE DRAWINGS

FIG. 2A depicts IAV-induced apoptosis is potentiated by EMAPII. HLMVEC were stimulated with 1 pfu/cell IAV in the presence of 30 ug/ml recombinant EMAPII, then analyzed for cleaved caspase 3 levels. $*p<0.05$ by one-way ANOVA with Tukey post-hoc.

FIG. 2B depicts IAV-induced apoptosis is potentiated by EMAPII. NHBEC were stimulated with 1 pfu/cell IAV in the presence of 30 ug/ml recombinant EMAPII, then analyzed for cleaved caspase 3 levels. $*p<0.05$ by one-way ANOVA with Tukey post-hoc.

FIG. 2C depicts IAV-induced apoptosis is potentiated by EMAPII and suppressed by EMAPII mAb. NHBEC were stimulated with 1 pfu/cell IAV in the presence of 10 µg/ml control IgG or EMAPII mAb, then analyzed for cleaved caspase 3 levels. *p<0.05 by one-way ANOVA with Tukey post-hoc.

DETAILED DESCRIPTION OF THE DISCLOSURE

Figure 1A:
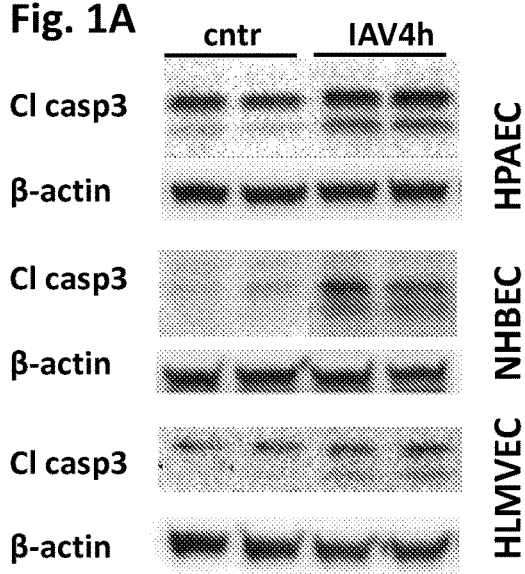
FIG. 1A depicts Western Blot analysis of Human pulmonary artery endothelial cells (HPAEC), normal human bronchial epithelial cells (NHBEC), and human lung microvascular endothelial cells (HLMVEC) that were stimulated with 1 pfu/cell IAV, and then analyzed for caspase 3 cleavage.

Endothelial-monocyte-activating protein (hereinafter referred to as EMAPII) is a monocyte- and endothelial cell-activating protein with prominent pro-apoptotic activity on endothelial cells. EMAPII has been established as a vascular endothelial cell (hereinafter referred to as EC) apoptosis-inducing and anti-angiogenic factor [4, 11]. EMAPII is secreted by epithelium, which is the primary target of lower respiratory infection by viruses such as Influenza A. It is also thought to promote inflammation based on its ability to recruit and activate monocytes [16, 12]. In the pulmonary vasculature development, EMAPII has been linked to the arrest of vascularization [13]. These characteristics make EMAPII plausible contributor to the development of lung injury and lung edema. A critical event leading to respiratory failure in acute respiratory distress syndrome (ARDS) is vascular leakage. Whereas barrier dysfunction due to activation of edemagenic pathways plays a pivotal role in initial edema development, endothelial cell (EC) apoptosis contributes to the sustained pulmonary damage.

Our invention directly addresses this area of need by providing a therapy which will block pro-apoptotic activity of endogenously expressed EMAPII. As EMAPII is a potential mediator of lung injury development in influenza-infected lungs, its ablation will attenuate vascular damage and facilitate lung recovery. We propose that anti-EMAPII antibodies prevent endothelial and epithelial apoptosis induced by EMAPII, either directly or via monocytes/macrophages-mediated signaling. Anti-EMAPII therapy would be a novel complementary treatment strategy to existing anti-viral and anti-inflammatory approaches.

While EMAPII involvement in barrier regulation is not yet documented, we have shown that rat anti-EMAPII monoclonal antibody (hereinafter referred to as "mAb") limits Influenza A virus (IAV)-induced weight loss, impairment of blood oxygenation, and lung edema in a murine model of IAV-induced lung injury without effect on inflammatory cell recruitment. For example, data summarized in the Examples below clearly demonstrate that therapy with EMAPII monoclonal antibody attenuates weight loss, impairment of blood oxygenation, and lung edema. Collectively, these data suggest that EMAPII is critically involved in pathogenesis of lower respiratory infection with IAV. Moreover, we detected a reduced level of EMAPII in bronchoalveolar lavage fluid (herein after referred to as BALF), which suggests that EMAPII levels are therapeutically tractable using a mAb strategy.

Without being bound to any particular theory or mechanism of action, EMAPII neutralizing antibodies will be useful to improve survival and to reduce recovery time from IAV. Moreover, EMAPII-neutralizing antibodies limit apoptosis and vascular leakage induced by IAV-induced lower respiratory infection. Since EMAPII-neutralizing antibody reduce lung edema, such antibodies will be useful to complement existing anti-inflammatory treatments. Of note, while anti-inflammatory treatment options are well established, there is no real treatment for edema occurring due to endothelial and epithelial cell death. Further, our results show that EMAPII-neutralizing antibodies shift the inflammatory response from a pro-inflammatory M1 to an anti-inflammatory M2-like macrophage phenotype, demonstrated by the reduction in TNF-α expression and an increase expression of CD206 and YM1.

In one embodiment, a method of treating or preventing endothelial or epithelial lung damage is provided. The method comprises administering a therapeutically effective amount of an EMAPII-neutralizing antibody or EMAPII-binding portion thereof to a subject having or suspected of having a lower respiratory tract influenza A virus infection, whereby endothelial or epithelial lung damage is treated or prevented.

The term "treating" "or "treatment" of endothelial or epithelial lung damage encompasses, but is not limited to, reducing, inhibiting or preventing the apoptosis and cell death of endothelial and/or epithelial lung cells, inhibiting or preventing decreased blood oxygenation and reducing, inhibiting or preventing lung edema, and/or reducing, inhibiting or preventing inflammation in the lung.

The terms "effective amount" or "therapeutically effective amount" refer to an amount sufficient to effect beneficial or desirable biological and/or clinical results.

The term "antibody" as used herein also includes an "antigen-binding portion" of an antibody. The term "antigen-binding portion," as used herein, refers to one or more fragments of an antibody that retain the ability to specifically bind to an antigen (e.g., polypeptide or fragment thereof of EMAPII) and block signaling through the EMAPII pathway. Examples of binding fragments encompassed within the term "antigen-binding portion" of an antibody include, but are not limited to, (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al, (1989) Nature 341:544-546), which consists of a VH domain; and (vi) an isolated complementarily determining region (CDR). Antibody fragments, including single-chain antibodies, may comprise the variable region(s) alone or in combination with the entirety or a portion of the following: hinge region, CHL CH2, and CH3 domains.

Antibodies used in the methods may be polyclonal or monoclonal; xenogeneic, allogeneic, or syngeneic; or modified forms thereof (e.g., humanized, chimeric, etc.). A Suitable antibodies may be fully human or humanized. Preferably, antibodies of the invention bind specifically or substantially specifically to the antigen (e.g. EMAPII, polypeptides or fragments thereof). The term "monoclonal antibodies" refers to a population of antibody polypeptides that contain only one species of an antigen binding site capable of binding a particular epitope of an antigen, whereas the term "polyclonal antibodies" refers to a population of antibody polypeptides that contain multiple species of antigen binding sites capable of interacting with a particular antigen.

Suitable neutralizing antibodies are able to inhibit or reduce at least one biological activity of the antigen (e.g. EMAPII) it binds. In certain embodiments, the neutralizing antibodies or fragments thereof substantially or completely inhibit a given biological activity of EMAP II.

Suitable EMAPII monoclonal antibodies can be made as described in Clauss M, Voswinckel R, Rajashekhar G, et al. Lung endothelial monocyte-activating protein 2 is a mediator of cigarette smoke-induced emphysema in mice. The Journal of clinical investigation 2011; 121: 2470-2479, and Rajashekhar G, et al. A monoclonal rat anti-mouse EMAP II antibody that functionally neutralizes pro- and mature-EMAP II in vitro. J Immunol Methods. 2009; 350(1-2):22-28, and are disclosed in U.S. Patent Publication No. 20140221607 entitled "Monoclonal Antibodies and Antigens for Diagnosing and Treating Lung Disease and Injury" filed Jun. 8, 2013, the contents of which are incorporated by reference in their entireties. Some aspects of the invention include EMAP-II neutralizing antibodies, comprising: a heavy chain, wherein said heavy chain includes the heavy chain hypervariable regions CDR1, CDR2 and CDR3, wherein CDR1 includes at least a portion of the polypeptide according to SEQ. ID. NO. 5, CDR2 includes at least a portion of the polypeptide according to SEQ. ID. NO. 6, and CDR3 includes at least a portion of the polypeptide according to SEQ. ID. NO. 7; and a light chain, wherein said light chain includes the light chain hypervariable regions $CDR1_L$ $CDR2_L$ and $CDR3_L$ wherein $CDR1_L$ includes at least a portion of the polypeptide according to SEQ. ID. NO. 8, $CDR2_L$ includes at least a portion of the polypeptide according to SEQ. ID. NO. 9 and $CDR3_L$ includes at least a portion of the polypeptide according to SEQ. NO. 10, wherein the heavy chain and the light chain form a portion of a humanized antibody, that binds to human EMAPII. In some embodiments, CDR1 is SEQ. ID. NO. 5, CDR2 is SEQ. ID. NO. 6, and CDR3 is SEQ. ID. NO. 7; and $CD1_L$ is SEQ. ID. NO. 8, $CDR2_L$ is SEQ. ID. NO. 9, and $CDR3_L$ is SEQ. ID. NO. 10. In one embodiment, the neutralizing anti-EMAP II antibody is a rat monoclonal neutralizing antibody M7 against mouse EMAP II as described in the above references. The rat monoclonal neutralizing antibody M7 against mouse EMAP II was developed by immunizing Lewis rats with recombinant murine pro-EMAP II. Lymphocytes isolated from the spleen and lymph nodes of immunized rats were fused with the mouse myeloma SP2/0, and clones were selected by testing hybridoma supernatants in enzyme-linked immunosorbent assays (ELISAs) for binding both pro- and mature EMAP II. The clones most active in ELISA were further characterized by Western blotting and neutralization of EMAP II-induced endothelial apoptosis in tissue culture experiments.

Within the antigen-binding portion of an antibody, as is well-known in the art, there are complementarity-determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity-determining regions (CDR1 through CDR3). The CDRs, and in particular the CDR3 regions, and more particularly the heavy chain CDR3, are largely responsible for antibody specificity. It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies. A "humanized monoclonal antibody" as used herein is a human monoclonal antibody or functionally active fragment thereof having human constant regions and a binding CDR3 region from a mammal of a species other than a human. Humanized monoclonal antibodies may be made by any method known in the art. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.).

European Patent Application 0239400, the entire contents of which is hereby incoporated by reference, provides an exemplary teaching of the production and use of humanized monoclonal antibodies in which at least the CDR portion of a murine (or other non-human mammal) antibody is included in the humanized antibody. Human monoclonal antibodies may be made by any of the methods known in the art, such as those disclosed in U.S. Pat. No. 5,567,610, issued to Borrebaeck et al., U.S. Pat. No. 5,565,354, issued to Ostberg, U.S. Pat. No. 5,571,893, issued to Baker et al, Kozbor D et al., J Immunol 133:3001-5 (1984), Brodeur et al., Monoclonal Antibody Production Techniques and Applications, pp. 51-63 (Marcel Dekker, Inc, New York, 1987), and Boerner P et al., J Immunol 147:86-95 (1991). In addition to the conventional methods for preparing human monoclonal antibodies, such antibodies may also be prepared by immunizing transgenic animals that are capable of producing human antibodies (e.g., Jakobovits A et al., Proc Natl Acad Sci USA 90:2551-5 (1993); Jakobovits A et al., Nature 362:255-8 (1993); Bruggermann et al., Year in Immunology 7:33 (1993); and U.S. Pat. No. 5,569,825 issued to Lonberg).

Endothelial or epithelial lung damage can be selected from the group consisting of weight loss, impairment of blood oxygenation, and lung edema.

In some embodiments, the neutralizing antibody is administered in combination with the Standard of Care treatment for Influenza A viral infection, for example, the antiviral osteltamivir.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a mammalian, for example, human, subject. The subject is suitably suffering from a lower respiratory infection, more preferably a lower respiratory tract influenza A virus infection.

A method of reducing or preventing endothelial or epithelial cell apoptosis in the lung of a subject, the method comprising administering a therapeutically effective amount of an EMAPII-neutralizing antibody, EMAPII-neutralizing antibody fragment, or EMAPII-binding portion thereof to a subject to reduce or prevent endothelial or epithelial cell apoptosis. In some aspects, the subject has or is suspected of having a lower respiratory influenza A virus infection.

The methods disclosed herein can include a conventional treatment regimen, which can be altered to include the steps of the methods described herein. The methods disclosed herein can include monitoring the patient to determine efficacy of treatment and further modifying the treatment in response to the monitoring. The methods disclosed herein can include administering a therapeutically effective amount of at least one EMAPII-neutralizing antibody or portions thereof.

A method of resolving or reducing inflammation in the lung of a subject having or suspected of having a lower respiratory tract infection are provided. The method comprises increasing the anti-inflammatory M2-like macrophage phenotype in the lung of the subject by administering a therapeutically effective amount of an EMAPII-neutralizing antibody, or EMAPII-binding portion thereof to the subject. This method also increases the amount of regulatory T cells (T-regs) in the lung of the subject which in turn resolves or reduced the inflammation associated with the respiratory infection. Regulatory T cells (Tregs) are Foxp3+CD4+ suppressive T cell subset which play an important role in the regulation of an immune response. Tregs are known to play a role in a number of immune system functions, including, but not limited to, suppression of pathogen-induced immunopathology, downregulation of effector class of the immune response, suppression of T-cell activation by weak stimuli, feedback control of the magnitude of the immune response by effector Th cells, and prevention of autoimmune diseases by establishing and maintaining immunologic self-tolerance, among others. The increase of Tregs plays a role in the resolving and/or reducing inflammation in the lung of a subject suffering a lower respiratory track infection In some embodiments, the increase in anti-inflammatory M2-like macrophage phenotype comprises an increase in expression of at least one M2-like macrophage marker. Suitable M2-like macrophage marker include, but are not limited to, for example, IL10, CD206, and YM1.

In some embodiments, the method of resolving or reducing inflammation in the lung further comprises a reduction in the pro-inflammatory M1 macrophage phenotype. Suitably, in some embodiments, there is a reduction in the expression of TNF-α in the lung of the subject.

The present invention has been described in terms of one or more preferred embodiments, and it should be appreciated that many equivalents, alternatives, variations, and modifications, aside from those expressly stated, are possible and within the scope of the invention.

The following non-limiting examples are included for purposes of illustration only, and are not intended to limit the scope of the range of techniques and protocols in which the compositions and methods of the present invention may find utility, as will be appreciated by one of skill in the art and can be readily implemented.

EXAMPLE

Role of EMAPII in Influenza A Virus (IAV) Pathology

Influenza infections are associated with the risk of development of lower respiratory tract infections, pneumonia, and lung injury [1] [2]. Current treatment of influenza infections relies primarily on neuraminidase inhibitors, which are most effective when given within first 48 hours [3]. As with any anti-viral, the development of resistance due to constant mutation of virus remains a possibility [4]. Therefore, there is an unmet medical need for a therapy which will protect lung by modulating host responses rather than targeting specific virus replication.

EMAPII is a pro-apoptotic, pro-inflammatory factor released by endothelial cells (EC) and epithelium in response to stress stimuli [11, 16]. EMAPII levels increase in chronic lung inflammatory conditions such as COPD; EMAPII monoclonal antibodies (mAb) limits development of emphysematous changes in mice exposed to cigarette smoke [12]. EMAPII is known to induce EC apoptosis and is also released by EC apoptosis inducers, such as hypoxia [13].

In this example, we demonstrate that EMAPII is released in response to influenza A virus (IAV) in vitro and in vivo. Importantly, we demonstrate that EMAPII ablation with mAb attenuates EMAPII levels and limits IAV-induced apoptosis and lung injury in mice.

First, we demonstrated that IAV induces EMAPII release and apoptosis in endothelial and epithelial cells. We have also shown that IAV-induced lung damage in mice is associated with EMAPII release to bronchoalveolar lavage fluid (BALF), concomitant with increases in caspase 3 activity. Injection of monoclonal antibody (mAb) against EMAPII reduced IAV-induced EMAPII levels, weight loss, reduction of blood oxygenation, lung edema, and increase of pro-inflammatory cytokine TNF alpha. Levels of caspase 3 activity in BALF were also decreased by mAb treatment. Moreover, we have detected EMAPII mAb-induced increase in markers for M2-like macrophages, YM1 and CD206, in lung. We have also detected EMAPII mAb-induced increase in marker for T-regulatory cells, FoxP3. Altogether, these data strongly suggest that EMAPII mAb ameliorates IAV-induced lung injury by limiting lung cell apoptosis, and shifting host inflammatory venue toward resolution of inflammation.

Results

Figure 1B:
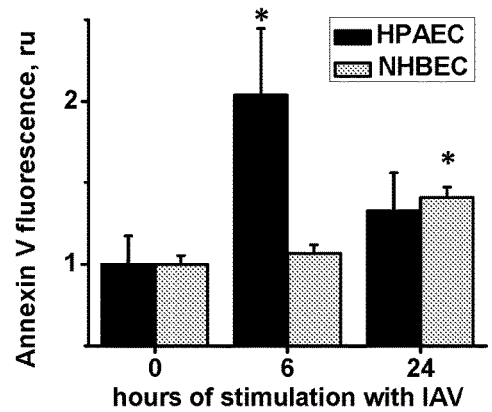
FIG. 1B depicts analysis of HPAEC and NHBEC that were stimulated with 1 pfu/cell IAV and then analyzed for surface annexin V staining. $*p<0.05$ by t-test when compared to control values.
Figure 1C:
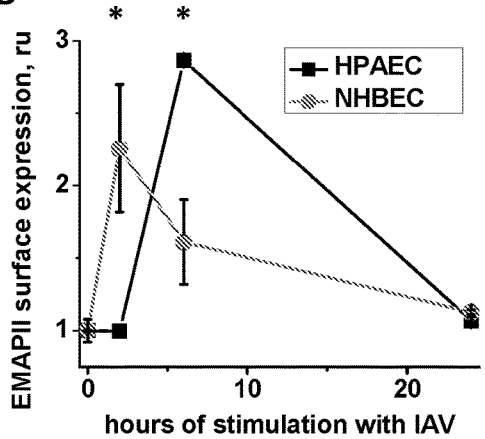
FIG. 1C depicts analysis of HPAEC and NHBEC that were stimulated with 1 pfu/cell IAV and then analyzed for surface EMAPII staining. $*p<0.05$ by t-test when compared to control values.
Figure 1D:
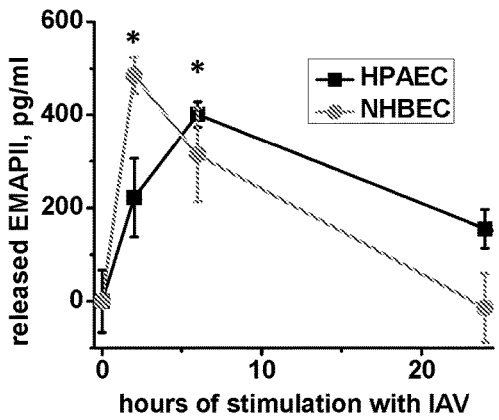
FIG. 1D depicts results of HPAEC or NHBEC stimulated with 1 pfu/cell IAV and media analyzed by EMAPII ELISA. $*p<0.05$ by t-test when compared to control values.
Figure 1E:
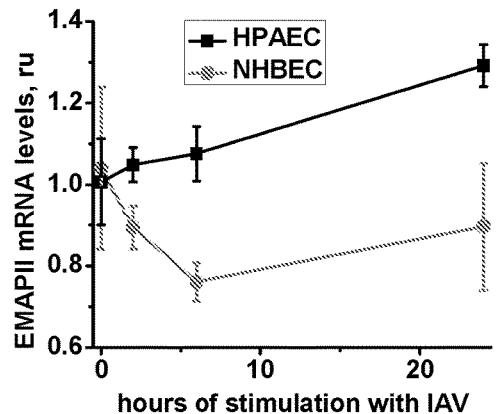
FIG. 1E depicts analysis of HPAEC and NHBEC that were stimulated with 1 pfu/cell IAV and then analyzed for EMAPII mRNA levels. $*p<0.05$ by t-test when compared to control values.

IAV induces EMAPII-dependent apoptosis in pulmonary endothelium and epithelium: IAV evokes caspase 3 cleavage and increases surface annexin V staining in pulmonary endothelial and epithelial cells, evident of apoptosis (FIG. 1A). Bronchial pulmonary endothelial cells and both macro- and microvascular endothelial cells respond to IAV with caspase 3 cleavage observed as early as 4 h post-infection (FIG. 1A). Consistently, surface annexin V staining is increased in IAV-infected epithelium and endothelium (FIG. 1B). We next studied whether IAV induces EMAPII release in these cells. We observed early relocation of EMAPII to the cell surface (FIG. 1C) and release of extracellular EMAPII (FIG. 1D) in endothelium and epithelium. These early events were not accompanied by the concomitant increase in EMAPII mRNA levels (FIG. 1E). To show that EMAPII release contributes to IAV-induced apoptosis, we first compared caspase cleavage in cells treated with IAV in the presence and absence of recombinant EMAPII. EMAPII enhanced IAV-induced caspase 3 cleavage in HLMVEC, potentiating IAV effect (FIG. 2A). Importantly, neutralization of extracellular EMAPII with EMAPII mAb, but not control IgG, reduced IAV-induced apoptosis (FIG. 2B).

Figure 3A:
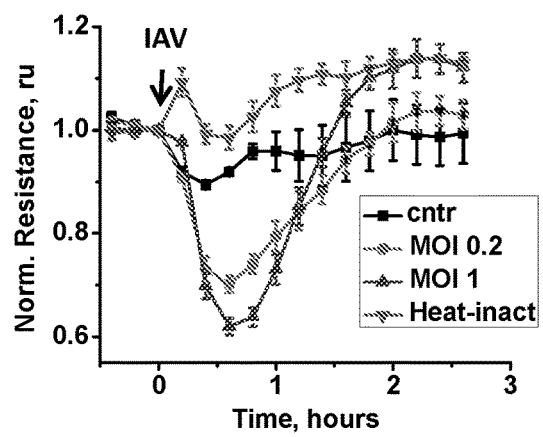
FIG. 3A depicts IAV-induced hyperpermeability in endothelial monolayers. HLMVEC grown to confluence were stimulated with indicated amounts of IAV, or heat-inactivated IAV (MOI 1). Shown are mean±SE of 3 parallel recordings.
Figure 3B:
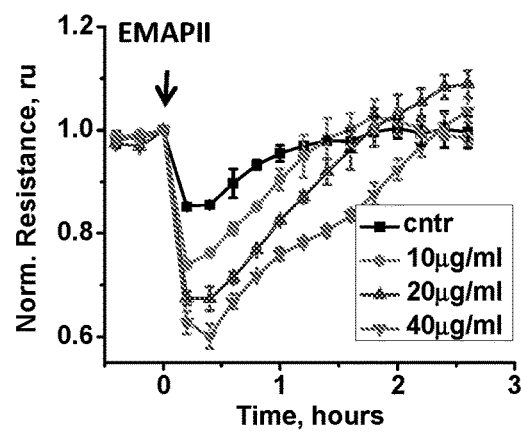
FIG. 3B depicts EMAPII-induced hyperpermeability in endothelial monolayers. HLMVEC grown to confluence were stimulated with indicated amounts of recombinant EMAPII. Shown are mean±SE of 3 parallel recordings.
Figure 3C:
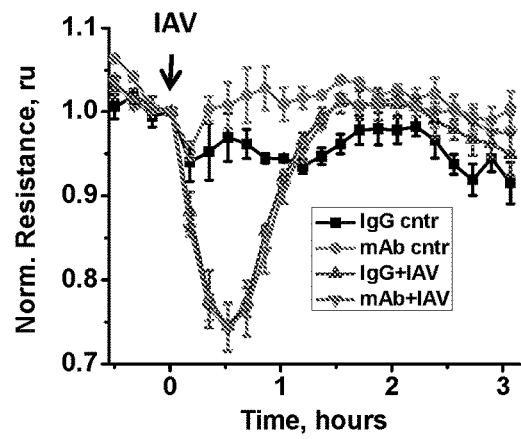
FIG. 3C depicts IAV-induced hyperpermeability in endothelial monolayers. HPAEC grown to confluence were pre-treated with 10 µg/ml control IgG or EMAPII mAb for 24 h, then stimulated with IAV MOI 1 in the presence of 10 µg/ml control IgG or EMAPII mAb, Shown are mean±SE of 3 parallel recordings.

IAV and EMAPII induce barrier dysfunction in pulmonary endothelium. To further study role of EMAPII in IAV-induced lung injury, we assessed IAV and EMAPII effects on transendothelial permeability. HLMVEC monolayers challenged with 0.3-3 MOI of IAV responded with transient decrease of transendothelial resistance (FIG. 3A). Control treatment with heat-inactivated virus did not generate hyperpermeability response, suggesting that active virus is required to induce barrier dysfunction. EMAPII evoked similar hyperpermeability response in HLMVEC, showing dose dependence in the range of 10 to 40 ug/ml (FIG. 3B).

Figure 4A:
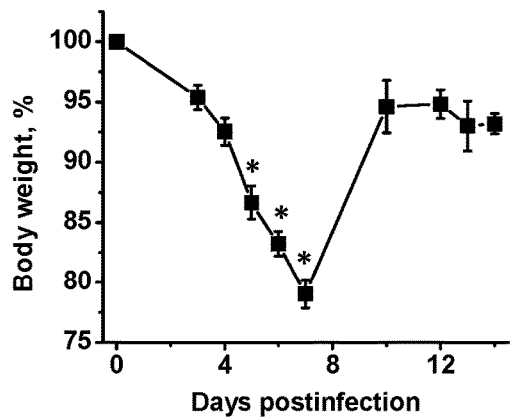
FIG. 4A depicts results of mice administered 750 pfu/mouse IAV to lung and analyzed for weight loss. *p<0.05 by ANOVA with Tukey post-hoc when compared to control values. N=5 for control group and 3-4 for all other groups.
Figure 4B:
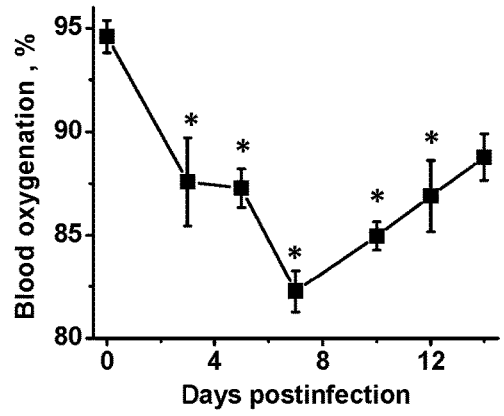
FIG. 4B depicts results of mice administered 750 pfu/mouse IAV to lung and analyzed for conscious blood oxygenation. *p<0.05 by ANOVA with Tukey post-hoc when compared to control values. N=5 for control group and 3-4 for all other groups.
Figure 4C:
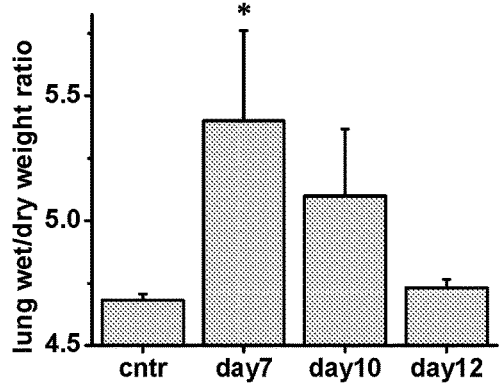
FIG. 4C depicts results of mice administered 750 pfu/mouse IAV to lung and analyzed for lung edema. *p<0.05 by ANOVA with Tukey post-hoc when compared to control values. N=7 for control group and 3-4 for all other groups.
Figure 4D:
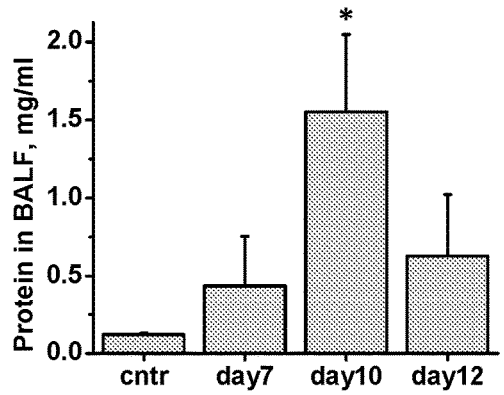
FIG. 4D depicts results of mice administered 750 pfu/mouse IAV to lung and analyzed for BALF protein extravasation. *p<0.05 by ANOVA with Tukey post-hoc when compared to control values. N=7 for control group and 3-4 for all other groups.
Figure 4E:
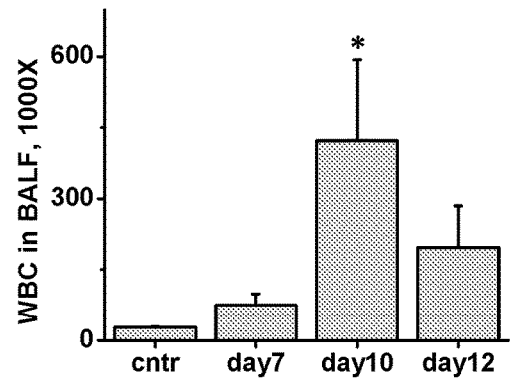
FIG. 4E depicts results of mice administered 750 pfu/mouse IAV to lung and analyzed for BALF white blood cell (WBC) count. *p<0.05 by ANOVA with Tukey post-hoc when compared to control values.
Figure 5A:
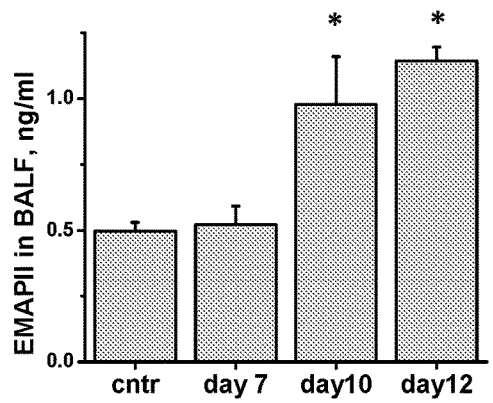
FIG. 5A shows results of mice administered 750 pfu/mouse IAV to lung and analyzed for BALF level of EMAPII. *p<0.05 by ANOVA with Tukey post-hoc when compared to control values. N=7 for control group and 3-4 for all other groups.
Figure 5B:
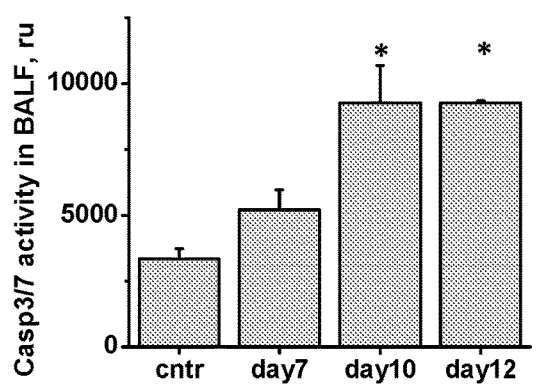
FIG. 5B shows results of mice administered 750 pfu/mouse IAV to lung and analyzed for BALF level of caspase 3/7 activity *p<0.05 by ANOVA with Tukey post-hoc when compared to control values. N=7 for control group and 3-4 for all other groups.
Figure 5C:
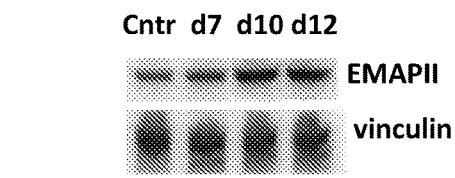
FIG. 5C shows results of mice administered 750 pfu/mouse IAV to lung and analyzed for lung levels of EMAPII. *p<0.05 by ANOVA with Tukey post-hoc when compared to control values. N=7 for control group and 3-4 for all other groups.
Figure 5C:
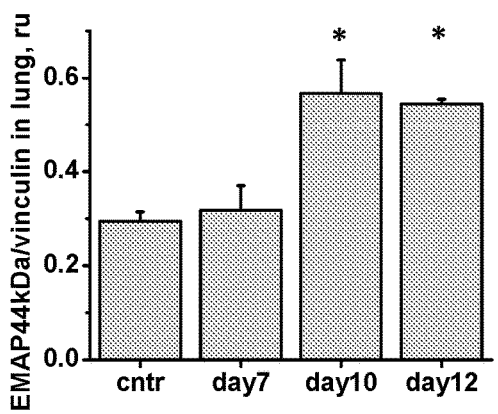
Figure 5D:
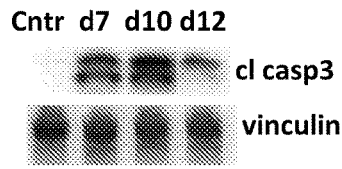
FIG. 5D shows results of mice administered 750 pfu/mouse IAV to lung and analyzed for lung levels of cleaved caspase 3. *p<0.05 by ANOVA with Tukey post-hoc when compared to control values. N=7 for control group and 3-4 for all other groups.
Figure 5D:
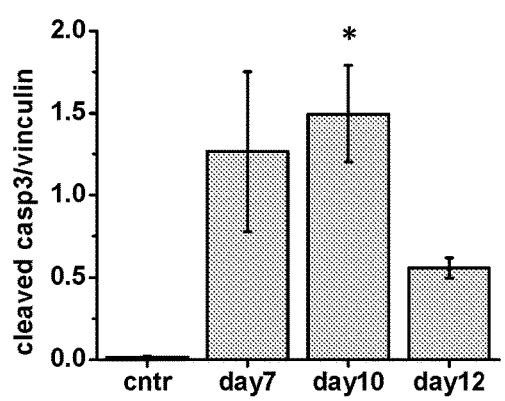

IAV lung injury is associated with increase in EMAPII levels and apoptosis in lung:

To properly time therapeutic intervention with EMAPII mAb, we first studied model of IAV lung infection in detail. Delivery of 750 pfu of IAV to mouse lung caused a self-limiting infection in mice, characterized by an initial decrease in body weight reaching 88% of the original weight at day 7, and followed by a spontaneous restoration to 95% of the original weight at day 10-14 (FIG. 4A). Consistent with the course of malaise, conscious blood oxygenation decreased from 95% at day 0 to 82% at day 7, recovering to 90% by day 14 (FIG. 4B). Assessment of ARDS indices showed that lung edema peaked at day 7 (FIG. 4C), whereas inflammatory cell and protein extravasation in bronchoalveolar lavage fluid (BALF) were greater at day 10 (FIG. 4D, E). Importantly, we have shown that IAV-induced lung injury was associated with EMAPII release to BALF and increase in EMAPII expression in lung (FIGS. 5A, B). No increase in EMAPII plasma concentration was noted (data not shown). Consistent with pro-apoptotic role of EMAPII, IAV-induced increase in caspase 3 activity in BALF and lung was concomitant with increase in EMAPII total and released levels (FIG. 5C, D).

Figure 6A:
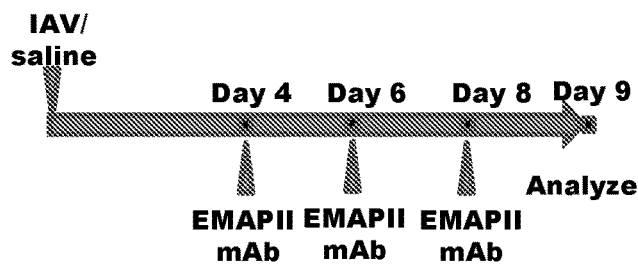
FIG. 6A is a schematic depicting subcutaneous injections schedule for injections of mice which received 750 pfu/mouse IAV or equal volume of saline (cntr). Half of IAV-infected mice were treated with EMAP II mAb (2 mg/kg) on days 4, 6, and 8 post-infection.
Figure 6B:
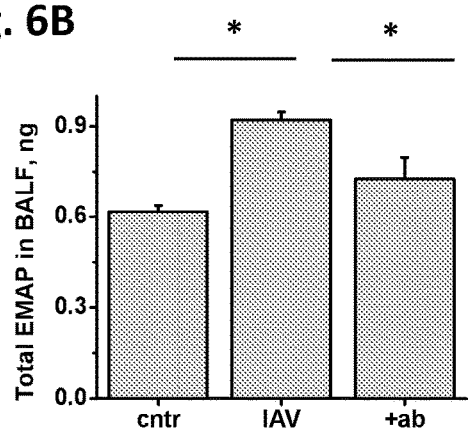
FIG. 6B is a bar graph depicting results mice analyzed for EMAPII levels in BALF after protocol of FIG. 6A. *p<0.05 by ANOVA with Tukey post-hoc. N=5 for all groups.
Figure 6C:
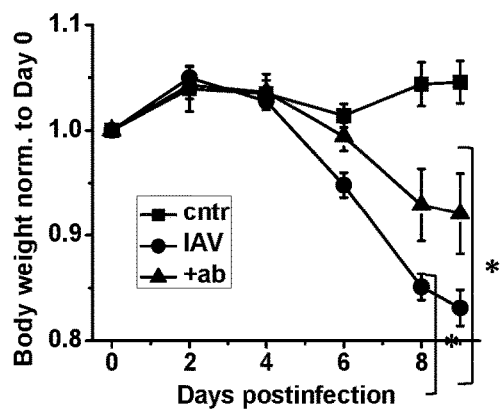
FIG. 6C is a line graph depicting results of mice analyzed for IAV-induced weight loss, (D) conscious blood oxygenation, (E) lung edema (day 9), (F) BALF caspase 3/7 activity (day 9). *p<0.05 by Repeated Measurements ANOVA. N=5 for all groups.
Figure 6D:
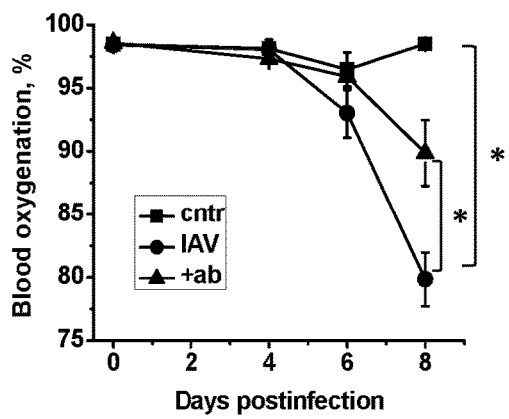
FIG. 6D is a line graph depicting results of mice analyzed for conscious blood oxygenation. *p<0.05 by ANOVA with Tukey post-hoc. N=5 for all groups.

EMAPII mAb attenuate released EMAPII levels and limit lung injury and apoptosis: To assess whether EMAPII ablation is able to limit IAV-induced lung injury, we timed EMAPII mAb administration to prevent EMAPII release and raise of ARDS indices in IAV-infected lung (FIG. 6A); day 9 post-infection was chosen for terminal analyses. Repeated subcutaneous injections of EMAPII mAb attenuated the levels of EMAPII released to BALF (FIG. 6B). As expected, total levels of EMAPII in lung tissue of mAb-treated mice did not change significantly (data not shown). Importantly, EMAPII mAb ameliorated IAV-induced loss of body weight (FIG. 6C), decreased blood oxygenation (FIG.

Figure 6E:
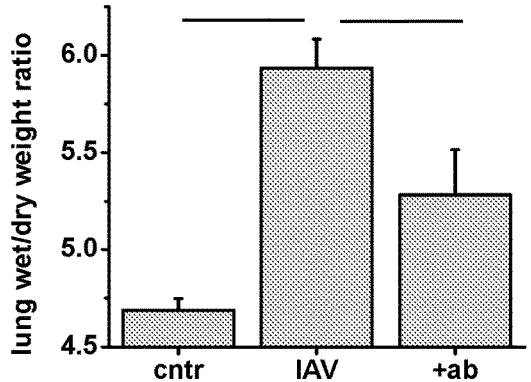
FIG. 6E is a bar graph depicting results of mice analyzed for lung edema (day 9). *p<0.05 by ANOVA with Tukey post-hoc. N=5 for all groups.
Figure 6F:
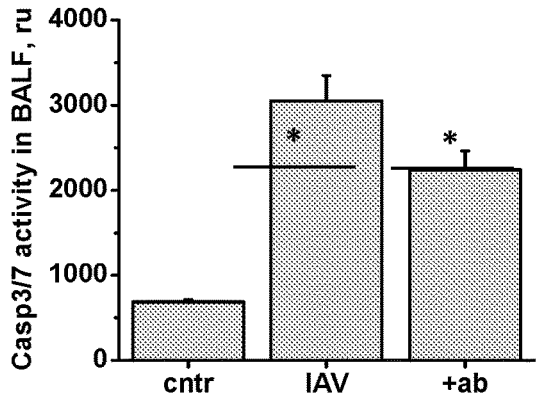
FIG. 6F is a bar graph depicting results of mice analyzed for BALF caspase 3/7 activity (day 9). *p<0.05 by ANOVA with Tukey post-hoc. N=5 for all groups.
Figure 7A:
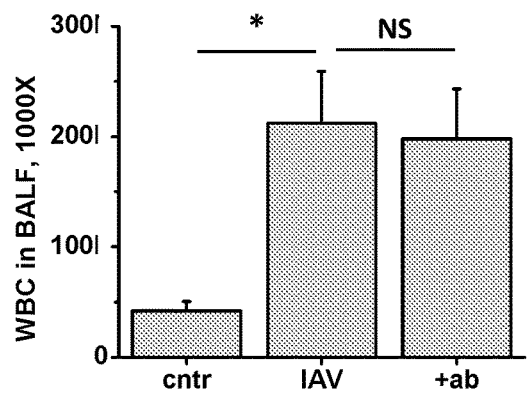
FIG. 7A depicts results of mice from FIG. 6 analyzed for total WBC count in BALF. *p<0.05 by ANOVA with Tukey post-hoc. N=5 for all groups.
Figure 7B:
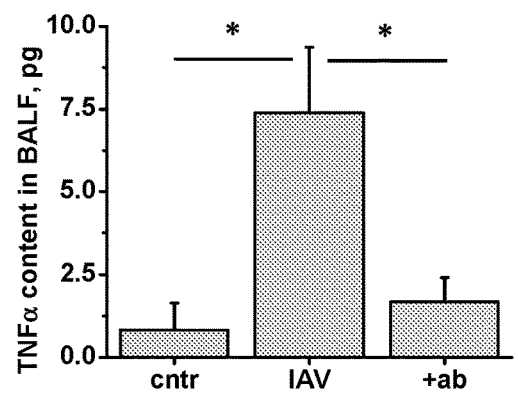
FIG. 7B depicts results of mice from FIG. 6 analyzed for TNFα levels in BALF. *p<0.05 by ANOVA with Tukey post-hoc. N=5 for all groups.

6D), and lung edema (FIG. 6E) in mice. EMAPII ablation with mAb significantly attenuated IAV-induced caspase 3 activity in BALF (FIG. 7A). To our surprise, EMAPII mAb therapy did not reduce the amount of inflammatory cell in BALF (FIG. 7B).

Figure 7C:
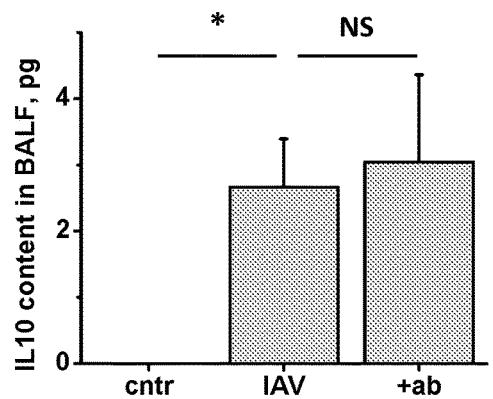
FIG. 7C depicts results of mice from FIG. 6 analyzed for IL10 levels in BALF. *p<0.05 by ANOVA with Tukey post-hoc. N=5 for all groups.
Figure 8A:
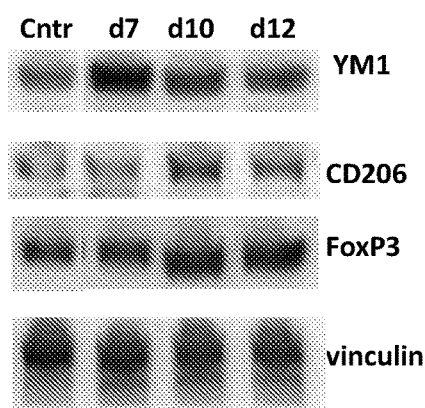
FIG. 8A depicts lung levels of YM1, CD206, and FoxP3 as detected in IAV-infected mice on the days indicated.
Figure 8B:
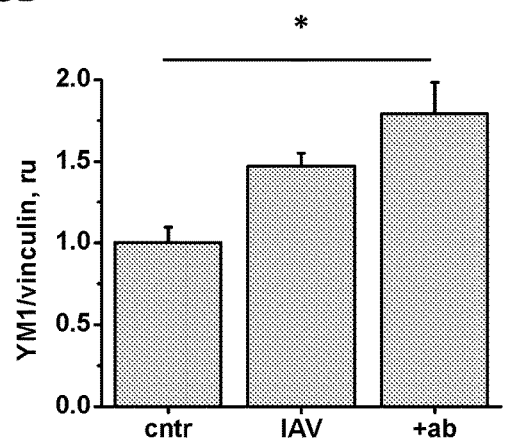
FIG. 8B depicts day 9 lung levels of YM1 in mice receiving EMAPII mAb therapy. *p<0.05 by ANOVA with Tukey post-hoc. N=5 for all groups.
Figure 8C:
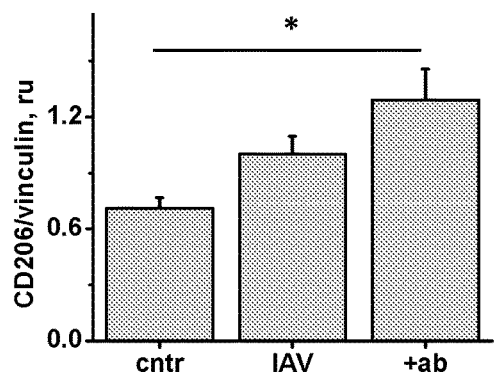
FIG. 8C depicts day 9 lung levels of CD206 in mice receiving EMAPII mAb therapy. *p<0.05 by ANOVA with Tukey post-hoc. N=5 for all groups.
Figure 8D:
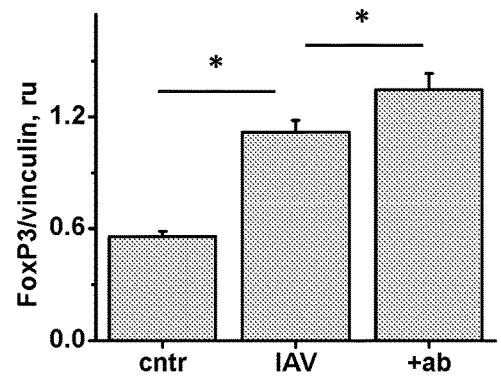
FIG. 8D depicts lung levels of FoxP3 in mice receiving EMAPII mAb therapy. *p<0.05 by ANOVA with Tukey post-hoc. N=5 for all groups.

EMAPII mAb promotes a change of inflammatory host venue in IAV-infected mice: To understand why attenuation of lung edema was seemingly independent of inflammation, we undertook further analysis of inflammatory cytokines and markers. Analysis of TNFα level in BALF revealed significant attenuation of this M1 macrophage marker in EMAPII mAb-treated mice (FIG. 7C), suggesting that mAb therapy does suppress pro-inflammatory venue in IAV-infected mice. Analysis of IL-10, an anti-inflammatory M2 macrophage marker, showed significantly increased IL-10 levels in IAV-treated mice independent of mAb treatment (FIG. 7D). To prove that spontaneous increase in M2 markers is consistent with self-limiting model of IAV infection, we analyzed levels of M2 markers YM1 and CD206 in lungs. Indeed, spontaneous increases of YM1 and CD206 levels at days 7-10 post-infection were noted in response to IAV (FIG. 8A). Importantly, YM1 and CD206 levels in mice receiving EMAPII mAb therapy were significantly higher than the levels detected in control mice (FIGS. 8B, C). Analysis of T-regulatory cell marker FoxP3 also showed a spontaneous increase at day 10 of IAV infection (FIG. 8A). This increase was significantly potentiated by EMAPII mAb therapy (FIG. 8D).

Discussion

Our study is the first to show that EMAPII-neutralizing antibodies can ameliorate IAV-induced lung injury in mice. Previously, EMAPII was proven to be a key pathological factor in chronic lung inflammatory condition such as COPD [12]. Here, we show that EMAPII contribute to the pathogenesis of acute inflammatory condition such as viral lung injury.

In vitro, we have shown that IAV causes release of extracellular EMAPII from endothelial and epithelial cells. EMAPII is able to activate pro-apoptotic pathways and cause barrier dysfunction in endothelium, contributing to pathogenesis of vascular leakage and lung edema. Importantly, we demonstrate here for the first time that EMAPII causes apoptosis in epithelial cells. Given the fact that apoptosis contributes to a variety of pathological conditions and diseases, careful investigation of EMAPII role in conditions when endothelium or epithelium are exposed to noxious stimuli may reveal yet undiscovered involvement of EMAPII in pathogenesis. For these conditions, EMAPII mAb therapy may be of clinical relevance.

In this report, we have shown that repeated subcutaneous administration of EMAPII mAb effectively limits IAV-induced body weight loss and lung injury indices including decreased blood oxygenation, lung edema, and levels of pro-inflammatory cytokine TNFα. Despite the fact that EMAPII increases in BALF were not detected until day 9-10 of IAV infection, administration of EMAPII mAb on day 4 allowed us to see improvement in body weight as early as day 6 post-infection. These data suggest that local EMAPII levels rise comparatively early in the course of IAV infection, and attenuation of these levels is of clinical significance.

In accordance with pro-apoptotic role of EMAPII [11] [12], we detected strong attenuation of caspase 3/7 activity in BALF of EMAPII mAb-treated mice. While the reduction of lung cell apoptosis likely attenuates lung edema, it is generally believed that recovery from pulmonary infections such as IAV also requires resolution of inflammation. To our surprise, initial assessment revealed no suppression of IAV-induced leukocyte extravasation by EMAPII mAb. However, our observation of reduced TNFα release in EMAPII mAb-treated animals prompted further investigation of the shift between the pro-inflammatory M1 and anti-inflammatory M2-like macrophage phenotype. Analysis of M2-like macrophage markers IL10, CD206 and YM1 revealed that their expression is spontaneously increased between day 7 and day 10 in the self-limiting model of IAV infection analyzed here. Importantly, CD206 and YM1 levels were further increased in mice receiving EMAPII mAb therapy. Similar to the levels of M2-like macrophage markers, level of T-regulatory cell marker FoxP3 also revealed further potentiation of the spontaneous IAV-induced increase. Both M2-like macrophages and T-reg cells were recently shown to play important roles in the resolution of lung injury [14, 15]. Altogether, our data clearly show that EMAPII mAb therapy exerts its beneficial effects via several mechanisms involving suppression of lung cell apoptosis as well as promotion of the resolution of inflammation.

In conclusion, this study has clearly shown that EMAPII mAb effectively attenuates IAV-induced lung injury in mice. This therapy targets a novel component of endothelial/epithelial injury along with more conventional component of host inflammatory venue. In contrast to existing anti-viral therapies and prospective therapies with virus-specific monoclonal antibodies, this therapy will not be subject to compromise by virus resistance and can be possibly extended to treat lung injury from other viruses frequently causing pulmonary complications, such as adenovirus.

Materials and Methods

Cell Culture

Human Pulmonary Artery Endothelial cells (HPAEC), human lung microvascular cells (HLMVEC) and normal human bronchial epithelial cells (NHBEC) (Lonza, Walkerville, Md.) were stimulated with H1N1 A/PR/8/34 (ATCC, Manassas, Va., #VR-1469) in the absence or presence of rat IgG (Abcam, Cambridge, UK, ab #37361) or rat anti-human EMAPII M7/1 mAb [12]. Media was analyzed with human AIMP1 competitive Elisa kit (MyBioSource, San Diego, Calif.). Cells were stained for surface proteins with anti-EMAPII mAb [12] or annexin V antibody (Abcam, #ab14085), and subjected to flow cytometry using a Calibur flow cytometer and Cell QuestPro software (BD Biosciences, San Jose Calif.), or analyzed for cell fluorescence using FlexStation II (Molecular Devices, Sunnyvale, Calif.). Mean fluorescence was assessed For EMAPII; percentage of positive cells was assessed for annexin V. For EMAPII mRNA level analysis, qRT-PCR was performed with EMAPII primers from Sino Biological Inc (Beijing, China), using β-actin as housekeeping gene. Alternatively, cells were digested with 1% SDS-containing PBS and analyzed by Western Blot with anti-cleaved caspase 3 (Cell Signaling, Danvers, Mass., #9664) and anti-β-actin antibodies (Sigma, St Louis, Mo., #A5441).

Animals

All animal procedures were approved by Indiana University Institutional Animal Care and Use Committee and conformed to the requirements of Animal Welfare Act.

To induce lung injury, 750 pfu/mouse of IAV were delivered to 12 week-old female C57B1/6 mice by oropharyngeal aspiration [13]. Two mg/kg rat anti-human EMAPII mAb [12] were administered subcutaneously on days 4, 6, and 8 post-infection. Blood oxygenation levels were measured in alert animals using MouseOx Plus neck sensor (Starr Life Sciences, Oakmont, Pa.). At sacrifice, lungs were collected and/or used to extract bronchoalveolar lavage (BALF).

BALF was obtained from anesthetized animals by flushing right lung with 3 portions of ice-cold PBS (0.8 ml). Left lung was excised and used for wet/dry weight analysis; right lung was snap-frozen and used for Western blot analyses. BALF was centrifuged at 600 g to sediment cells; pellet was subjected to red cell lysis; supernatant was frozen for future analyses. BALF supernatants were analyzed with Apo-one caspase 3/7 activity assay (Promega, Madison, Wis.), TNFα, and IL-10 ELISA (R&D Systems, Minneapolis, Minn.). Lung tissue was digested with 1% SDS (in PBS containing antiprotease cocktail) using beads homogenizer. Extracts were analyzed by Western Blotting with anti-YM1 (R&D Systems #AF2446), CD206 (Abcam #ab64693), FoxP3 (Abcam #ab20034), and vinculin (Abcam, #ab18058) antibodies.

Measurement of Transendothelial Permeability

Transendothelial electrical resistance (TER) was measured using the highly sensitive biophysical assay with an electrical cell-substrate impedance sensor as described previously.

Statistical Analysis

Quantitative data are presented as mean±SEM. Statistical analysis was performed by t-test, One-way ANOVA with Tukey post-hoc, or Repeated Measurements ANOVA using Origin 8.0 or GraphPad Prism6 software. A probability value of <0.05 was considered statistically significant.

REFERENCES

1. Nair H, Brooks W A, Katz M, et al. Global burden of respiratory infections due to seasonal influenza in young children: a systematic review and meta-analysis. *Lancet* (London, England) 2011; 378:1917-1930.
2. Mertz D, Kim T H, Johnstone J, et al. Populations at risk for severe or complicated influenza illness: systematic review and meta-analysis. *BMJ (Clinical research ed)* 2013; 347:f5061.
3. Hsu J, Santesso N, Mustafa R, et al. Antivirals for treatment of influenza: a systematic review and meta-analysis of observational studies. Annals of internal medicine 2012; 156:512-524.
4. Bank S. New treatments for influenza. *BMC medicine* 2012; 10:104.
5. Hayden F G, de Jong M D. Emerging influenza antiviral resistance threats. *The Journal of infectious diseases* 2011; 203:6-10.
6. van der Vries E, Stittelaar K J, van Amerongen G, et al. Prolonged influenza virus shedding and emergence of antiviral resistance in immunocompromised patients and ferrets. *PLoS pathogens* 2013; 9:e1003343.
7. Ecker D M, Jones S D, Levine H L. The therapeutic monoclonal antibody market. *mAbs* 2015; 7:9-14.
8. Barnett G, Jakobsen A M, Tas M, et al. Prostate adenocarcinoma cells release the novel proinflammatory polypeptide EMAP-II in response to stress. *Cancer research* 2000; 60: 2850-2857.
9. Green L A, Yi R, Petrusca D, et al. HIV envelope protein gp120-induced apoptosis in lung microvascular endothelial cells by concerted upregulation of EMAP II and its receptor, CXCR3. *Am J Physiol Lung Cell Mol Physiol* 2014; 306: L372-382.
10. Knies U E, Behrensdorf H A, Mitchell C A, et al. Regulation of endothelial monocyte-activating polypeptide II release by apoptosis. *Proc Natl Acad Sci USA* 1998; 95: 12322-12327.
11. Schwarz M A, Kandel J, Brett J, et al. Endothelial-monocyte activating polypeptide II, a novel antitumor cytokine that suppresses primary and metastatic tumor growth and induces apoptosis in growing endothelial cells. *The Journal of experimental medicine* 1999; 190:341-354.
12. Clauss M, Voswinckel R, Rajashekhar G, et al. Lung endothelial monocyte-activating protein 2 is a mediator of cigarette smoke-induced emphysema in mice. *The Journal of clinical investigation* 2011; 121:2470-2479.
13. Zhang S, Danchuk S D, Imhof K M, et al. Comparison of the therapeutic effects of human and mouse adipose-derived stem cells in a murine model of lipopolysaccharide-induced acute lung injury. *Stem Cell Res Ther* 2013; 4:13.
14. D'Alessio F R, Craig J M, Singer B D, et al. Enhanced Resolution of Experimental ARDS through IL-4-Mediated Lung Macrophage Reprogramming. *Am J Physiol Lung Cell Mol Physiol* 2016: ajplung.00419.02015.
15. D'Alessio F R, Tsushima K, Aggarwal N R, et al. CD4+CD25+Foxp3+ Tregs resolve experimental lung injury in mice and are present in humans with acute lung injury. *The Journal of clinical investigation* 2009; 119:2898-2913.
16. Schwarz, R. E. and M. A. Schwarz, In vivo therapy of local tumor progression by targeting vascular endothelium with EMAP-II. J Surg Res, 2004. 120(1): p. 64-72.

We claim:

1. A method of treating virus-induced acute lung injury in a subject having influenza, the method comprising administering a therapeutically effective amount of an EMAPII-neutralizing antibody or EMAPII-binding portion thereof to a subject having a lower respiratory tract influenza A infection, whereby the acute lung injury is treated, wherein the EMAPII-neutralizing antibody or binding portion thereof comprises a heavy chain comprising heavy chain hypervariable regions CDR1 of SEQ ID NO:5, CDR2 or SEQ ID NO:6, and CDR3 of SEQ ID NO:7, and a light chain comprising light chain hypervariable regions CDR1 of SEQ ID NO:8, CDR2 of SEQ ID NO:9, and CDR3 of SEQ ID NO:10, and wherein the virus-induced acute lung injury is selected from the group consisting of pneumonia, impairment of blood oxygenation, and lung edema.

2. The method of claim 1, wherein the EMAPII-neutralizing antibody is co-administered with one or more agents selected from the group consisting of an anti-inflammatory agent and an anti-viral agent.

3. The method of claim 1, wherein the subject is a mammal.

4. The method of claim 3, wherein the subject is a human.

5. The method of claim 1, wherein the EMAPII-neutralizing antibody is a monoclonal antibody.

6. The method of claim 1, wherein the EMAPII neutralizing antibody is an EMAPII specific Fab fragment.

7. A method of reducing endothelial or epithelial cell apoptosis associated with influenza-induced acute lung injury in the lung of a subject having a lower respiratory viral infection, the method comprising administering a therapeutically effective amount of an EMAPII-neutralizing antibody, EMAPII-neutralizing antibody fragment, or EMAPII-binding portion thereof to a subject to reduce endothelial or epithelial cell apoptosis associated with virus-induced acute lung injury, wherein the EMAPII-neutralizing antibody or binding portion thereof comprises a heavy chain comprising heavy chain hypervariable regions CDR1 of SEQ ID NO:5, CDR2 or SEQ ID NO:6, and CDR3 of SEQ ID NO:7, and a light chain comprising light chain hypervariable regions CDR1 of SEQ ID NO:8, CDR2 of SEQ ID NO:9, and CDR3 of SEQ ID NO:10.

8. The method of claim 7, wherein the lower respiratory viral infection is an influenza A virus infection.

9. The method of claim 7, wherein the EMAPII-neutralizing antibody is a monoclonal antibody.

10. The method of claim 7, wherein the EMAPII neutralizing antibody is a Fab fragment.

11. The method of claim 7, wherein the subject is a mammal.

12. The method of claim 7, wherein the subject is a human.

13. A method of reducing inflammation in the lung of a subject having influenza-induced acute lung injury by increasing the anti-inflammatory macrophage phenotype and decreasing the pro-inflammatory macrophage expressing M2 markers in the lung of the subject, the method comprising administering a therapeutically effective amount of an EMAPII-neutralizing antibody, EMAPII-neutralizing antibody fragment, or EMAPII-binding portion thereof to a subject having a lower respiratory tract influenza A virus infection, wherein there is an increase in anti-inflammatory macrophage phenotype and a decrease in pro-inflammatory macrophage phenotype, wherein the EMAPII-neutralizing antibody or binding portion thereof comprises a heavy chain comprising heavy chain hypervariable regions CDR1 of SEQ ID NO:5, CDR2 or SEQ ID NO:6, and CDR3 of SEQ ID NO:7, and a light chain comprising light chain hypervariable regions CDR1 of SEQ ID NO:8, CDR2 of SEQ ID NO:9, and CDR3 of SEQ ID NO:10.

14. The method of claim 12, wherein the increase in anti-inflammatory macrophage phenotype comprises an increase in expression of at least one anti-inflammatory macrophage marker, the at least one anti-inflammatory macrophage marker selected from the group consisting of IL10, CD206, and YM1.

15. The method of claim 13, wherein the reduction in the pro-inflammatory-macrophage phenotype comprises reduction in the expression of TNF-$\alpha$.

* * * * *

SEQUENCE LISTING

<160> NUMBER OF SEQ ID NOS: 15

<210> SEQ ID NO 1
<211> LENGTH: 354
<212> TYPE: DNA
<213> ORGANISM: Rattus rattus

<400> SEQUENCE: 1
gcggtgcacc ttgttgagtc tggtggagga tttgtgcagc ctacggagtc attgaaaatc        60
tcatgtgcag cctctggatt caccttcagt gatgctgcca tgtactgggt ccgccaggct       120
ccaggaaagg gtctggaatg ggttgctcgc ataagaacta aacctaataa ttatgcaaca       180

```
tattatgctg attcagtgaa aggcagattc accatctccc gagatgattc aaaaagcatg    240
gtctacctac aaatggataa cttgaaaact gaggacacag ccatgtatta ctgtacatca    300
tggagctacg actttgatta ctggggccaa ggagtcatgg tcacagtctc ctca          354
```

<210> SEQ ID NO 2
<211> LENGTH: 118
<212> TYPE: PRT
<213> ORGANISM: Rattus rattus

<400> SEQUENCE: 2

```
Ala Val His Leu Val Glu Ser Gly Gly Gly Phe Val Gln Pro Thr Glu
1               5                   10                  15

Ser Leu Lys Ile Ser Cys Ala Ala Ser Gly Phe Thr Phe Ser Asp Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Tyr Tyr Ala Asp
    50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Thr Glu Asp Thr Ala Met Tyr
                85                  90                  95

Tyr Cys Thr Ser Trp Ser Tyr Asp Phe Asp Tyr Trp Gly Gln Gly Val
            100                 105                 110

Met Val Thr Val Ser Ser
        115
```

<210> SEQ ID NO 3
<211> LENGTH: 112
<212> TYPE: PRT
<213> ORGANISM: Rattus rattus

<400> SEQUENCE: 3

```
Asp Ile Val Met Thr Gln Gly Ala Leu Pro Asn Pro Val Pro Ser Gly
1               5                   10                  15

Glu Ser Ala Ser Ile Thr Cys Gln Ser Ser Lys Ser Leu Leu His Ser
            20                  25                  30

Ser Gly Lys Thr Tyr Leu Asn Trp Tyr Leu Gln Arg Pro Gly Gln Ser
        35                  40                  45

Pro His Leu Leu Ile Tyr Trp Met Ser Thr Arg Ala Ser Gly Val Ser
    50                  55                  60

Asp Arg Leu Ser Gly Ser Gly Ser Gly Thr Asp Phe Thr Leu Lys Ile
65                  70                  75                  80

Ser Ser Val Glu Ala Glu Asp Val Gly Val Tyr Tyr Cys Gln Gln Phe
                85                  90                  95

Leu Glu Tyr Pro Leu Thr Phe Gly Ser Gly Thr Lys Leu Glu Ile Lys
            100                 105                 110
```

<210> SEQ ID NO 4
<211> LENGTH: 337
<212> TYPE: DNA
<213> ORGANISM: Rattus rattus

<400> SEQUENCE: 4

```
gatattgtga tgacccaggg tgcactcccc aaccctgtcc cctctggaga gtcagcttcc    60
atcacctgcc agtctagtaa gagtctgctg cacagcagtg gcaagacata cttgaattgg   120
```

```
tatctgcaga ggccaggaca gtctcctcat ctcctgatct attggatgtc cacccgtgca    180
tcaggagtct cagacaggct cagtggcagt gggtcaggaa cagatttcac actgaaaatc    240
agcagcgtgg aggctgagga tgtgggtgtg tattactgtc agcaatttct agagtatcct    300
ctcacgttcg gttctgggac caagctggag atcaaac                             337
```

<210> SEQ ID NO 5
<211> LENGTH: 8
<212> TYPE: PRT
<213> ORGANISM: Rattus rattus

<400> SEQUENCE: 5

Gly Phe Thr Phe Ser Asp Ala Ala
1               5

<210> SEQ ID NO 6
<211> LENGTH: 10
<212> TYPE: PRT
<213> ORGANISM: Rattus rattus

<400> SEQUENCE: 6

Ile Arg Thr Lys Pro Asn Asn Tyr Ala Thr
1               5                   10

<210> SEQ ID NO 7
<211> LENGTH: 9
<212> TYPE: PRT
<213> ORGANISM: Rattus rattus

<400> SEQUENCE: 7

Thr Ser Trp Ser Tyr Asp Phe Asp Tyr
1               5

<210> SEQ ID NO 8
<211> LENGTH: 11
<212> TYPE: PRT
<213> ORGANISM: Rattus rattus

<400> SEQUENCE: 8

Lys Ser Leu Leu His Ser Ser Gly Lys Thr Tyr
1               5                   10

<210> SEQ ID NO 9
<211> LENGTH: 3
<212> TYPE: PRT
<213> ORGANISM: Rattus rattus

<400> SEQUENCE: 9

Trp Met Ser
1

<210> SEQ ID NO 10
<211> LENGTH: 9
<212> TYPE: PRT
<213> ORGANISM: Rattus rattus

<400> SEQUENCE: 10

Gln Gln Phe Leu Glu Tyr Pro Leu Thr
1               5

<210> SEQ ID NO 11
<211> LENGTH: 69
<212> TYPE: PRT
<213> ORGANISM: Homo sapiens

<400> SEQUENCE: 11

Gln Gln Ser Ile Ala Gly Ser Ala Asp Ser Lys Pro Ile Asp Val Ser
1               5                   10                  15

Arg Leu Asp Leu Arg Ile Gly Cys Ile Ile Thr Ala Arg Lys His Pro
            20                  25                  30

Asp Ala Asp Ser Leu Tyr Val Glu Glu Val Asp Val Gly Glu Ile Ala
        35                  40                  45

Pro Arg Thr Val Val Ser Gly Leu Val Asn His Val Pro Leu Glu Gln
    50                  55                  60

Met Gln Asn Arg Met
65

<210> SEQ ID NO 12
<211> LENGTH: 17
<212> TYPE: PRT
<213> ORGANISM: Homo sapiens

<400> SEQUENCE: 12

Gln Gln Ser Ile Ala Gly Ser Ala Asp Ser Lys Pro Ile Asp Val Ser
1               5                   10                  15

Arg

<210> SEQ ID NO 13
<211> LENGTH: 17
<212> TYPE: PRT
<213> ORGANISM: Homo sapiens

<400> SEQUENCE: 13

Lys His Pro Asp Ala Asp Ser Leu Tyr Val Glu Glu Val Asp Val Gly
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: synthetic

<400> SEQUENCE: 14

Val Leu Lys Arg Leu Glu Gln Lys Gly Ala Glu Ala Asp Gln Ile Ile
1               5                   10                  15

Glu

<210> SEQ ID NO 15
<211> LENGTH: 672
<212> TYPE: PRT
<213> ORGANISM: Homo sapiens

<400> SEQUENCE: 15

Met Leu Pro Ala Val Ala Val Ser Glu Pro Val Val Leu Arg Phe Met
1               5                   10                  15

Ile Phe Cys Arg Leu Leu Ala Lys Met Ala Asn Asn Asp Ala Val Leu
            20                  25                  30

Lys Arg Leu Glu Gln Lys Gly Ala Glu Ala Asp Gln Ile Ile Glu Tyr
        35                  40                  45

Leu Lys Gln Gln Val Ser Leu Leu Lys Glu Lys Ala Ile Leu Gln Ala
    50                  55                  60

```
Thr Leu Arg Glu Glu Lys Lys Leu Arg Val Glu Asn Ala Lys Leu Lys
 65                  70                  75                  80

Lys Glu Ile Glu Glu Leu Lys Gln Glu Leu Ile Gln Ala Glu Ile Gln
                 85                  90                  95

Asn Gly Val Lys Gln Ile Pro Phe Pro Ser Gly Thr Pro Leu His Ala
            100                 105                 110

Asn Ser Met Val Ser Glu Asn Val Ile Gln Ser Thr Ala Val Thr Thr
        115                 120                 125

Val Ser Ser Gly Thr Lys Glu Gln Ile Lys Gly Gly Thr Gly Asp Glu
130                 135                 140

Lys Lys Ala Lys Glu Lys Ile Glu Lys Lys Gly Glu Lys Lys Glu Lys
145                 150                 155                 160

Lys Gln Gln Ser Ile Ala Gly Ser Ala Asp Ser Lys Pro Ile Asp Val
                165                 170                 175

Ser Arg Leu Asp Leu Arg Ile Gly Cys Ile Ile Thr Ala Arg Lys His
            180                 185                 190

Pro Asp Ala Asp Ser Leu Tyr Val Glu Val Asp Val Gly Glu Ile
        195                 200                 205

Ala Pro Arg Thr Val Val Ser Gly Leu Val Asn His Val Pro Leu Glu
210                 215                 220

Gln Met Gln Asn Arg Met Val Ile Leu Leu Cys Asn Leu Lys Pro Ala
225                 230                 235                 240

Lys Met Arg Gly Val Leu Ser Gln Ala Met Val Met Cys Ala Ser Ser
                245                 250                 255

Pro Glu Lys Ile Glu Ile Leu Ala Pro Pro Asn Gly Ser Val Pro Gly
            260                 265                 270

Asp Arg Ile Thr Phe Asp Ala Phe Pro Gly Glu Pro Asp Lys Glu Leu
        275                 280                 285

Asn Pro Lys Lys Lys Ile Trp Glu Gln Ile Gln Pro Asp Leu His Thr
290                 295                 300

Asn Asp Glu Cys Val Ala Thr Tyr Lys Gly Val Pro Phe Glu Val Lys
305                 310                 315                 320

Gly Lys Gly Val Cys Arg Ala Gln Thr Met Ser Asn Ser Gly Ile Lys
                325                 330                 335

Met Leu Pro Ala Val Ala Val Ser Glu Pro Val Val Leu Arg Phe Met
            340                 345                 350

Ile Phe Cys Arg Leu Leu Ala Lys Met Ala Asn Asn Asp Ala Val Leu
        355                 360                 365

Lys Arg Leu Glu Gln Lys Gly Ala Glu Ala Asp Gln Ile Ile Glu Tyr
370                 375                 380

Leu Lys Gln Gln Val Ser Leu Leu Lys Glu Lys Ala Ile Leu Gln Ala
385                 390                 395                 400

Thr Leu Arg Glu Glu Lys Lys Leu Arg Val Glu Asn Ala Lys Leu Lys
                405                 410                 415

Lys Glu Ile Glu Glu Leu Lys Gln Glu Leu Ile Gln Ala Glu Ile Gln
            420                 425                 430

Asn Gly Val Lys Gln Ile Pro Phe Pro Ser Gly Thr Pro Leu His Ala
        435                 440                 445

Asn Ser Met Val Ser Glu Asn Val Ile Gln Ser Thr Ala Val Thr Thr
        450                 455                 460

Val Ser Ser Gly Thr Lys Glu Gln Ile Lys Gly Gly Thr Gly Asp Glu
465                 470                 475                 480

Lys Lys Ala Lys Glu Lys Ile Glu Lys Lys Gly Glu Lys Lys Glu Lys
```

```
                    485                 490                 495
Lys Gln Gln Ser Ile Ala Gly Ser Ala Asp Ser Lys Pro Ile Asp Val
            500                 505                 510

Ser Arg Leu Asp Leu Arg Ile Gly Cys Ile Ile Thr Ala Arg Lys His
        515                 520                 525

Pro Asp Ala Asp Ser Leu Tyr Val Glu Glu Val Asp Val Gly Glu Ile
    530                 535                 540

Ala Pro Arg Thr Val Val Ser Gly Leu Val Asn His Val Pro Leu Glu
545                 550                 555                 560

Gln Met Gln Asn Arg Met Val Ile Leu Leu Cys Asn Leu Lys Pro Ala
                565                 570                 575

Lys Met Arg Gly Val Leu Ser Gln Ala Met Val Met Cys Ala Ser Ser
                580                 585                 590

Pro Glu Lys Ile Glu Ile Leu Ala Pro Pro Asn Gly Ser Val Pro Gly
        595                 600                 605

Asp Arg Ile Thr Phe Asp Ala Phe Pro Gly Glu Pro Asp Lys Glu Leu
        610                 615                 620

Asn Pro Lys Lys Ile Trp Glu Gln Ile Gln Pro Asp Leu His Thr
625                 630                 635                 640

Asn Asp Glu Cys Val Ala Thr Tyr Lys Gly Val Pro Phe Glu Val Lys
                645                 650                 655

Gly Lys Gly Val Cys Arg Ala Gln Thr Met Ser Asn Ser Gly Ile Lys
                660                 665                 670
```